(12) United States Patent
Stella et al.

(10) Patent No.: US 7,411,032 B2
(45) Date of Patent: Aug. 12, 2008

(54) METHOD FOR MAKING POLYETHERIMIDES

(75) Inventors: Albert Santo Stella, Voorheesville, NY (US); David Bruce Hall, Ballston Lake, NY (US)

(73) Assignee: SABIC Innovative Plastics IP B.V., Pittsfield, MA (US)

( * ) Notice: Subject to any disclaimer, the term of this patent is extended or adjusted under 35 U.S.C. 154(b) by 95 days.

(21) Appl. No.: 11/603,523

(22) Filed: Nov. 21, 2006

(65) Prior Publication Data

US 2007/0073035 A1 Mar. 29, 2007

Related U.S. Application Data

(63) Continuation-in-part of application No. 11/234,022, filed on Sep. 23, 2005, now abandoned.

(51) Int. Cl.
*C08G 69/26* (2006.01)
(52) U.S. Cl. ...................................... 528/350
(58) Field of Classification Search .............. 528/350; 549/241
See application file for complete search history.

(56) References Cited

U.S. PATENT DOCUMENTS

| 4,870,194 A | 9/1989 | Molinaro et al. |
| 4,906,760 A | 3/1990 | Mueller et al. |
| 5,081,298 A | 1/1992 | Brunelle |
| 5,145,971 A | 9/1992 | Lesins |
| 6,028,203 A | 2/2000 | Brunelle et al. |
| 6,706,897 B1 * | 3/2004 | Brunelle et al. ............. 549/241 |
| 6,727,370 B1 | 4/2004 | Brunelle et al. |

FOREIGN PATENT DOCUMENTS

EP 1674443 6/2006

OTHER PUBLICATIONS

Elliott P. Barrett et al., "The Determination of Pore Volume and Area Distributions in Porous Substances. I. Computations From Nitrogen Isotherms", Contribution from the Multiple Fellowship of Baugh and Sons Company, Mellon Institute, vol. 73, pp. 373-380, Jan. 1951.

* cited by examiner

*Primary Examiner*—Rebecca L Anderson
*Assistant Examiner*—Yong Chu

(57) ABSTRACT

A method for making polyetherimides is provided by reacting a high purity dianhydride with an aromatic diamine under condensation polymerization conditions. The dianhydrides employed are purified by a method comprising contacting a first solution containing a dianhydride compound, a solvent, and a phase transfer catalyst, with a solid inorganic adsorbent material having a total pore volume of about 0.5 milliliters/gram or greater and a cumulative pore volume distribution of about 20 percent or greater of particles having a pore diameter in a range between about 3 nanometers and about 20 nanometers. The solution containing the dianhydride compound is then separated from the solid inorganic adsorbent material to provide a purified dianhydride compound which is substantially free of the phase transfer catalyst. The purified dianhydrides are then condensed with aromatic diamines to provide polyetherimide compositions which are substantially free of residual phase transfer catalyst.

19 Claims, No Drawings

METHOD FOR MAKING POLYETHERIMIDES

This application is a Continuation-In-Part of U.S. patent application Ser. No. 11/234,022 entitled "Methods For Purifying Oxybisphthalic Compounds", filed Sep. 23, 2005.

BACKGROUND

The invention relates generally to the purification of dianhydrides and related bisimides. In one aspect the invention relates to the purification of dianhydrides and bisimides which are oxybisphthalic compounds. In a particular aspect, the invention relates to the purification of oxybisphthalic anhydrides.

Oxybisphthalic compounds, such as for example, oxybisphthalic anhydride (ODPA) are key raw materials used in preparation of polyetherimides. Bisimides related to ODPA, for example the N,N'-dimethylbisimide of ODPA, are useful intermediates in ODPA preparation. ODPA itself is a key monomer useful in the preparation of high temperature polyetherimides by condensation polymerization reaction with a diamine. In general, condensation polymerization processes require that the component monomers be of high purity in order to effectively build polymer molecular weight, obtain good reaction kinetics, and provide a thermally stable and processible polymer.

ODPA can be produced by the phase transfer catalyzed coupling of chlorophthalic anhydride in the presence of potassium carbonate and an organic phase transfer catalyst, such as hexaethylguanidinium chloride (HEGCl). Alternately, ODPA can be produced by hydrolysis of the related bisimide prepared in turn by phase transfer catalyzed coupling of an N-alkyl chlorophthalimide in the presence of potassium carbonate and an organic phase transfer catalyst, such as hexaethylguanidinium chloride (HEGCl). Although the coupling processes are efficient in the presence of the organic phase transfer catalyst, the product dianhydride or related bisimide may contain a significant fraction of the phase transfer catalyst employed, or its reaction and/or degradation products/adducts. Residual phase transfer catalyst has been shown to have an adverse effect on the thermal stability of polymers prepared using ODPA as a monomer or comonomer.

Therefore, there is a need for dianhydrides and related bisimides which are substantially free of residual phase transfer catalyst. Moreover, there is a need for more efficient methods for the separation of residual organic phase transfer catalysts from dianhydrides and related bisimides prepared using synthetic methods involving one or more reactions mediated by a phase transfer catalyst.

BRIEF DESCRIPTION

In one embodiment, the present invention provides a method of preparing a polyetherimide, said method comprising reacting at least one aromatic diamine with a purified dianhydride, said purified dianhydride having been purified by a method, said method comprising the steps of:
  (a) providing a first solution comprising at least one dianhydride, at least one solvent, and at least one organic phase transfer catalyst; and
  (b) contacting the first solution with a solid inorganic adsorbent material, said solid inorganic adsorbent material having a total pore volume of about 0.5 milliliters/gram or greater, and a cumulative pore volume distribution of about 20 percent or greater of particles having a pore diameter in a range between about 3 nanometers and about 20 nanometers; to provide a second solution of the dianhydride, which is substantially free of the organic phase transfer catalyst.

In another aspect, the present invention provides a method for purifying an oxybisphthalic anhydride having structure (IV),

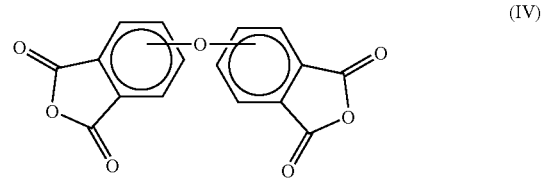

(IV)

The method comprises steps (a) and (b). In step (a), a first solution comprising at least one oxybisphthalic anhydride (IV), at least one solvent, and at least one organic phase transfer catalyst is provided. In step (b), the first solution is contacted with a solid inorganic adsorbent material, said solid inorganic adsorbent material having a total pore volume of about 0.5 milliliters/gram or greater, and a cumulative pore volume distribution of about 20 percent or greater of particles having a pore diameter in a range between about 3 nanometers and about 20 nanometers; to provide a second solution of the oxybisphthalic anhydride (IV), which is substantially free of the phase transfer catalyst.

In yet another aspect, the present invention provides a method for purifying an oxybisphthalic anhydride having structure (IV), the method comprising the steps of:
  (a) providing a first solution comprising at least one oxybisphthalic anhydride (IV), ortho-dichlorobenzene solvent, and a hexaalkylguanidinium halide phase transfer catalyst; and
  (b) contacting the first solution with a silica, said silica having a total pore volume of about 0.5 milliliters/gram or greater, and a cumulative pore volume distribution of about 20 percent or greater of particles having a pore diameter in a range between about 3 nanometers and about 20 nanometers; said contacting being carried out at a temperature in a range between about 50° C. and about 250° C. to provide a second solution of the oxybisphthalic anhydride (IV) which is substantially free of said phase transfer catalyst.

In a still another aspect, the present invention provides a method for preparing an oxybisphthalic anhydride having structure (IV). The method comprises steps (a)-(e). In step (a), at least one inorganic carbonate salt, at least one organic phase transfer catalyst, and at least one substituted phthalic compound having structure (VI),

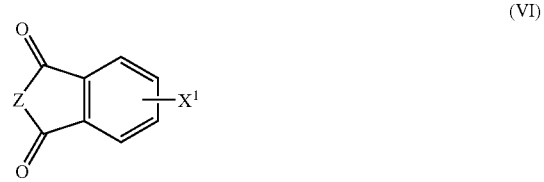

(VI)

wherein Z is oxygen; and $X^1$ is independently selected from the group consisting of fluoro, chloro, bromo, iodo, and nitro groups; are contacted to provide a first product mixture comprising the at least one organic phase transfer catalyst and the oxybisphthalic anhydride (IV). In Step (b) the first product mixture is diluted with at least one solvent to provide a second product mixture comprising the at least one organic phase transfer catalyst and the oxybisphthalic anhydride (IV). In step (c), substantially all of the oxybisphthalic anhydride (IV) present in the second product mixture is dissolved to provide a third product mixture, said third product mixture comprising less than 25 ppm water, and wherein said oxybisphthalic anhydride (IV) is present in an amount corresponding to less than 25 percent by weight of a total weight of the third product mixture. In step (d), the third product mixture is filtered at a temperature above the crystallization point temperature of the oxybisphthalic anhydride (IV) to provide a first solution of the oxybisphthalic anhydride (IV). In step (e), the first solution is contacted with a silica, said silica having a total pore volume of about 0.5 milliliters/gram or greater, and a cumulative pore volume distribution of about 20 percent or greater of particles having a pore diameter in a range between about 3 nanometers and about 20 nanometers; said contacting being carried out at a temperature in a range between about 50° C. and about 250° C. to provide a second solution of the oxybisphthalic anhydride (IV), which is substantially free of said phase transfer catalyst.

In other aspects, the present invention provides a purified oxybisphthalic anhydride having structure (IV) comprising less than about 150 parts per million of an organic phase transfer catalyst. The purified oxybisphthalic anhydrides provided by the present invention are useful in the preparation of polyetherimides.

These and other features, aspects, and advantages of the present invention may be more understood more readily by reference to the following detailed description.

DETAILED DESCRIPTION

In the following specification and the claims which follow, reference will be made to a number of terms which shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —$OPhC(CF_3)_2PhO$—), 4-chloromethylphen-1-yl, 3-trifluorovinyl-2-thienyl, 3-trichloromethylphen-1-yl (i.e., 3-$CCl_3Ph$—), 4-(3-bromoprop-1-yl)phen-1-yl (i.e., 4-$BrCH_2CH_2CH_2Ph$—), and the like. Further examples of aromatic radicals include 4-allyloxyphen-1-oxy, 4-aminophen-1-yl (i.e., 4-$H_2NPh$—), 3-aminocarbonylphen-1-yl (i.e., $NH_2COPh$—), 4-benzoylphen-1-yl, dicyanomethylidenebis(4-phen-1-yloxy) (i.e., —$OPhC(CN)_2PhO$—), 3-methylphen-1-yl, methylenebis(4-phen-1-yloxy) (i.e., —$OPhCH_2PhO$—), 2-ethylphen-1-yl, phenylethenyl, 3-formyl-2-thienyl, 2-hexyl-5-furanyl, hexamethylene-1,6-bis(4-phen-1-yloxy) (i.e., —$OPh(CH_2)_6PhO$—), 4-hydroxymethylphen-1-yl (i.e., 4-$HOCH_2Ph$—), 4-mercaptomethylphen-1-yl (i.e., 4-$HSCH_2Ph$—), 4-methylthiophen-1-yl (i.e., 4-$CH_3SPh$—), 3-methoxyphen-1-yl, 2-methoxycarbonylphen-1-yloxy (e.g., methyl salicyl), 2-nitromethylphen-1-yl (i.e., 2-$NO_2CH_2Ph$), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}C(CF_3)_2$$C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., $CH_3CHBrCH_2C_6H_{10}O$—), and the like. Further examples of cycloaliphatic radicals include 4-allyloxycyclohex-1-yl, 4-aminocyclohex-1-yl (i.e., $H_2NC_6H_{10}O$—), 4-aminocarbonylcyclopent-1-yl (i.e., $NH_2COC_5H_8$—), 4-acetyloxycyclohex-1-yl, 2,2-dicyanoisopropylidenebis(cyclohex-4-yloxy), (i.e., —$OC_6H_{10}C(CN)_2C_6H_{10}O$—), 3-methylcyclohex-1-yl, methylenebis(cyclohex-4-yloxy) (i.e., —$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —$OC_6H_{10}(CH_2)_6C_6H_{10}O$—), 4-hydroxymethylcyclohex-1-yl (i.e., 4-$HOCH_2C_6H_{10}$—), 4-mercaptomethylcyclohex-1-yl (i.e., 4-$HSCH_2C_6H_{10}$—), 4-methylthiocyclohex-1-yl (i.e., 4-$CH_3SC_6H_{10}$—), 4-methoxycyclohex-1-yl, 2-methoxycarbonylcyclohex-1-yloxy(2-$CH_3OCOC_6H_{10}O$—), 4-nitromethylcyclohex-1-yl (i.e., $NO_2CH_2C_6H_{10}$—), 3-trimethylsilylcyclohex-1-yl, 2-t-butyldimethylsilylcyclopent-1-yl, 4-trimethoxysilylethylcyclohex-1-yl (e.g., $(CH_3O)_3SiCH_2CH_2C_6H_{10}$—), 4-vinylcyclohexen-1-yl, vinylidenebis (cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl($C_4H_7O$—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —$CH_2CHBrCH_2$—), and the like. Further examples of aliphatic radicals include allyl, aminocarbonyl (i.e., —$CONH_2$), carbonyl, 2,2-dicyanoisopropylidene (i.e., —$CH_2C(CN)_2CH_2$—), methyl (i.e., —$CH_3$), methylene (i.e., —$CH_2$—), ethyl, ethylene, formyl (i.e., —CHO), hexyl, hexamethylene, hydroxymethyl (i.e., —$CH_2OH$), mercaptomethyl (i.e., —$CH_2SH$), methylthio (i.e., —$SCH_3$), methylthiomethyl (i.e., —$CH_2SCH_3$), methoxy, methoxycarbonyl (i.e., $CH_3OCO$—), nitromethyl (i.e., —$CH_2NO_2$), thiocarbonyl, trimethylsilyl (i.e., $(CH_3)_3Si$—), t-butyldimethylsilyl, 3-trimethyoxysilylpropyl (i.e., $(CH_3O)_3SiCH_2CH_2CH_2$—), vinyl, vinylidene, and the like. By way of further example, a $C_1$-$C_{10}$ aliphatic radical contains at least one but no more than 10 carbon atoms. A methyl group (i.e., $CH_3$—) is an example of a $C_1$ aliphatic radical. A decyl group (i.e., $CH_3(CH_2)_9$—) is an example of a $C_{10}$ aliphatic radical.

The present invention provides new and useful methodology for the purification of dianhydrides and related bisimides. It is believed that almost any dianhydride or related bisimide containing one or more organic phase transfer catalysts may be purified efficiently using the method of the present invention. By purified, it is meant that the dianhydride and/or the related bisimide may be separated from the phase transfer catalyst contaminant in such a manner such that the purified dianhydride and/or the related bisimide is substantially free of residual phase transfer catalyst.

While it is believed that the methods developed here are generally applicable to the purification of dianhydrides and related bisimides, the methods have been demonstrated to be especially effective in the removal of organic phase transfer catalysts from oxybisphthalic anhydrides and oxybisphthalimides, collectively referred to herein at times as oxybisphthalic compounds. Thus, in one embodiment, the present invention provides a method for purifying an oxybisphthalic compound having structure (I),

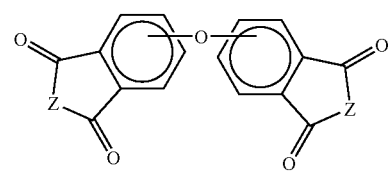

(I)

wherein Z is independently at each occurrence O or N—$R^1$, and $R^1$ is a $C_1$-$C_8$ aliphatic radical, a $C_3$-$C_{12}$ cycloaliphatic radical, or a $C_3$-$C_{12}$ aromatic radical; said method comprising the steps of:

(a) providing a first solution comprising at least one oxybisphthalic compound having structure (I), at least one solvent, and at least one organic phase transfer catalyst; and (b) contacting the first solution with a solid inorganic adsorbent material, said solid inorganic adsorbent material having a total pore volume of about 0.5 milliliters/gram or greater, and a cumulative pore volume distribution of about 20 percent or greater of particles having a pore diameter in a range between about 3 nanometers and about 20 nanometers; to provide a second solution of the oxybisphthalic compound having structure (I), which is substantially free of the organic phase transfer catalyst.

The term "providing a first solution comprising at least one oxybisphthalic compound having structure (I), at least one solvent, and at least one organic phase transfer catalyst" refers to any process by which the first solution comprising the oxybisphthalic compound, the solvent, and the organic phase transfer catalyst can be provided. Moreover, the scope of the term includes all the various methods by which the oxybisphthalic compound can be prepared. In an embodiment, the first solution is provided by dissolving a solid mixture comprising an oxybisphthalic compound and at least one organic phase transfer catalyst in at least one solvent. In another embodiment, the first solution is provided by reacting a halophthalic anhydride with potassium carbonate in a solvent, in the presence of at least one organic phase transfer catalyst to provide a mixture comprising an oxybisphthalic anhydride, potassium chloride, and said at least one phase transfer catalyst; and filtering said mixture to provide a first solution.

Non-limiting examples of oxybisphthalic compounds (I) include oxybisphthalimides having structure (II)

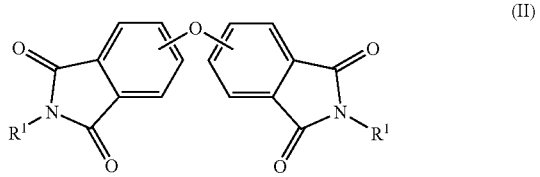

(II)

wherein $R^1$ is a $C_1$-$C_8$ aliphatic radical, a $C_3$-$C_{12}$ cycloaliphatic radical, or a $C_3$-$C_{12}$ aromatic radical. Non-limiting examples of such oxybisphthalimides having structure (II) include 4,4'-oxybis(N-methylphthalimide) (CAS No. 27507-54-6); 3,4'-oxybis(N-ethylphthalimide); 4,4'-oxybis(N-propylphthalimide); 3,3'-oxybis(N-butylphthalimide); 4,4'-oxybis(N-phenylphthalimide); 4,4'-oxybis[N-(ortho-tolyl)phthalimide]; 4,4'-oxybis(N-benzylphthalimide); 4,4'-oxybis(N-cyclopentylphthalimide); 3,4'-oxybis(N-cyclohexylphthalimide); and the like.

In a particular embodiment, the oxybisphthalic compound comprises 4,4'-oxybisphthalimide (III),

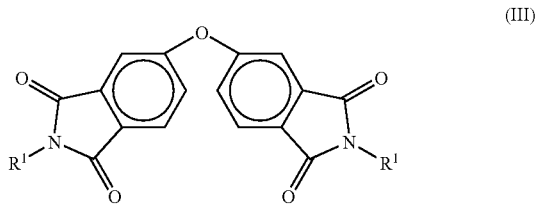

(III)

wherein $R^1$ is a $C_1$-$C_8$ aliphatic radical, a $C_3$-$C_{12}$ cycloaliphatic radical, or a $C_3$-$C_{12}$ aromatic radical. The oxybisphthalimides are useful in the preparation the corresponding oxybisphthalic anhydrides, which in turn are as precursors to the corresponding dianhydrides which are useful for preparing polyetherimides.

In one embodiment, the oxybisphthalic compound which can be purified by the method of the present invention is an oxybisphthalic anhydride having structure (IV).

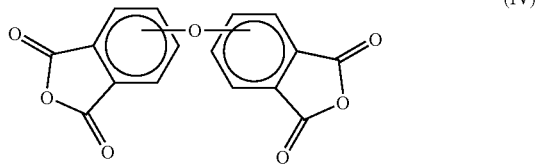

(IV)

Oxybisphthalic anhydride is hereinafter sometimes also referred to by the abbreviation "ODPA". Structure (IV) refers to the 3,4'-ODPA; 4,4'-ODPA; and 3,3'-ODPA isomers either singly or as mixtures containing two or more of 3,4'-ODPA; 4,4'-ODPA; and 3,3'-ODPA isomers. Each of the generic groups represented by generic structures I, II, and IV includes pure compounds as well as mixtures of compounds. For example, generic structure I may be used to represent a pure compound N,N'-di-t-butyl-4,4'-oxybisphthalimide. Alternately, generic structure I may be used to represent a mixture comprising N,N'-di-t-butyl-4,4'-oxybisphthalimide, N,N'-di-t-butyl-3,4'-oxybisphthalimide and N,N'-di-t-butyl-3,3'-oxybisphthalimide. Similarly, oxybisphthalic anhydride structure IV may be used to represent a single dianhydride, for example pure 4,4'-oxybisphthalic anhydride. Alternately generic structure IV may be used to represent a mixture comprising 4,4'-oxybisphthalic anhydride, 3,4'-oxybisphthalic anhydride, and 3,3'-oxybisphthalic anhydride. In one embodiment, structure IV represents an oxybisphthalic anhydride consisting essentially of 3,3'-oxybisphthalic anhydride. In an alternate embodiment, structure IV represents an oxybisphthalic anhydride consisting essentially of 3,4'-oxybisphthalic anhydride. In yet another embodiment, structure IV represents a mixture of 3,3'-oxybisphthalic anhydride and 3,4'-oxybisphthalic anhydride. In alternate embodiments, minor amounts (i.e., each of the "minor" components represents less than about less than about 5 percent by weight of the total weight of the composition) of the 3,3'-oxybisphthalic anhydride and 3,4'-oxybisphthalic anhydride are present in an oxybisphthalic anhydride consisting primarily of 4,4'-oxybisphthalic anhydride. In yet another embodiment, structure IV represents a oxybisphthalic anhydride isomer mixture consisting of about 49 percent by weight 4,4'-ODPA, about 42 percent by weight of 3,4'-ODPA and about 9 percent by weight of 3,3'-ODPA. In one embodiment, the oxybisphthalic anhydride represented as structure IV consists primarily of 4,4'-oxybisphthalic anhydride, a dianhydride having structure (V). As used herein, the term "consisting primarily of" refers to a composition having a major component that represents 90 percent by weight or more of the total weight of the composition.

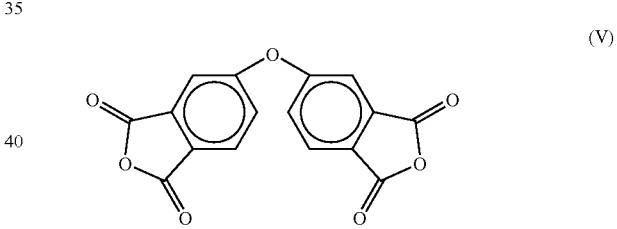

(V)

Compounds I-V can be prepared by methods known in the art, for example by reaction of a substituted phthalic compound VI,

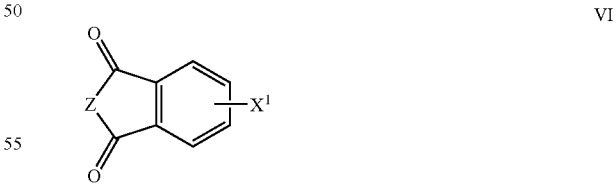

VI wherein "Z" is O or N—$R^1$, wherein $R^1$ is a $C_1$-$C_8$ aliphatic radical, a $C_3$-$C_{12}$ cycloaliphatic radical, or a $C_3$-$C_{12}$ aromatic radical; and $X^1$ is selected from the group consisting of fluoro, chloro, bromo, iodo, and nitro groups; with at least one inorganic carbonate salt, in at least one solvent, in the presence of at least one organic phase transfer catalyst. Aprotic solvents are generally used. Examples of solvents include chlorobenzene, ortho-dichlorobenzene, para-dichlorobenzene, dichlorotoluene, 1,2,4-trichlorobenzene, diphenyl sulfone, phenetole, anisole, veratrole, toluene, xylene, mesitylene, or mixtures thereof. The reaction provides a first product mixture comprising at least one oxybisphthalic compound I, an inorganic salt by-product, and the organic phase transfer catalyst. The reaction is typically carried out by heating the reactants and solvent in a stirred reactor. In one embodiment, the reaction mixture is heated to a temperature in a range from about 50° C. to about 250° C. The reactor can be equipped with a means for removing solvent by distillation, such as a distillation head, condenser, and receiver. Solvent may be distilled from the reaction mixture during the reaction or upon its completion as a means for removing adventitious water or water produced during the reaction. The product mixture typically comprises less than about 100 ppm of water as well. The identity of the salt by-product is determined by the inorganic carbonate employed as well as the nature of the substituent leaving group in the substituted phthalic anhydride ($X^1$ in structure VI). For example, when the substituted phthalic anhydride is 4-nitrophthalic anhydride and the inorganic carbonate is sodium carbonate, the salt by-product is sodium nitrite. As a further example, when the substituted phthalic anhydride is 4-chlorophthalic anhydride and the inorganic carbonate is potassium carbonate, the salt by-product is potassium chloride.

Suitable substituted phthalic compounds embraced by structure VI include substituted phthalimides and phthalic anhydrides. In one embodiment, a substituted phthalimide having structure VI wherein $Z=NR^1$, is used. Examples of suitable substituted phthalimides include substituted N-alkylphthalimides, substituted N-arylphthalimides, and substituted N-cycloalkylphthalimides, comprising a chlorine, fluorine, bromine, iodine, or nitro group in the 3- or the 4-position. These compounds can be prepared by reacting an aliphatic, aromatic, or cycloaliphatic primary amine with a phthalic anhydride substituted with a chlorine, fluorine, bromine, iodine, or nitro group in the 3- or the 4-position. Some examples of substituted phthalic anhydrides include, 3-chlorophthalic anhydride, 4-chlorophthalic anhydride, 3-fluorophthalic anhydride, 4-fluorophthalic anhydride, 4-nitrophthalic anhydride, 3-nitrophthalic anhydride, and mixtures thereof. Chlorophthalic compounds are frequently used since they are easily prepared from readily available starting materials. Alkali metal carbonates are commonly used as the inorganic carbonate salt. For example, 4,4'-ODPA can be produced by the coupling of 4-chlorophthalic anhydride using potassium carbonate as the inorganic carbonate salt and an organic phase transfer catalyst, for example a hexaalkylguanidinium halide salt such as hexaethylguanidinium chloride (HEGCl). The inorganic by-product under such conditions is the corresponding alkali metal chloride.

Organic phase transfer catalysts (PTC's) are known in the art. Reference is made, for example, to U.S Pat. No. 5,081, 298. Typical phase transfer catalysts include hexaalkylguanidinium salts, pyridinium salts, phosphazenium salts and the like. Representative hexaalkylguanidinium salts are illustrated by formula (VII). Representative pyridinium salts are illustrated by formula (VII). Representative phosphazenium catalysts are illustrated by formula (IX).

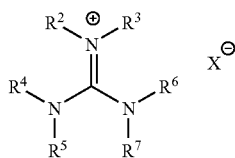
(VII)

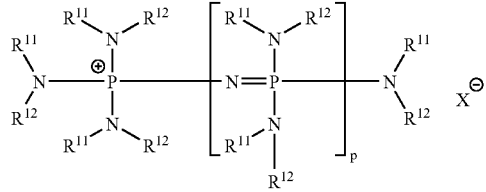
(VIII)

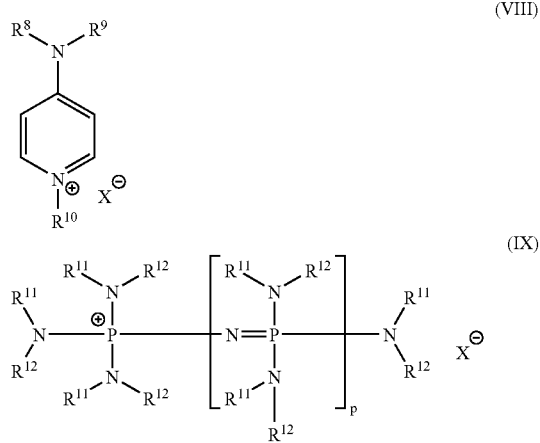
(IX)

In structures (VII), (VI) and (IX), the groups $R^2$-$R^{12}$ are independently a $C_1$-$C_{20}$ aliphatic radical, a $C_3$-$C_{40}$ aromatic radical, or a $C_3$-$C_{20}$ cycloaliphatic radical; and X– is a monovalent inorganic anion, a monovalent organic anion, a polyvalent inorganic anion, a polyvalent organic anion, or a mixture thereof. With respect to structure (IX), "p" is 0 or an integer from 1 to 10. In structures (VII), (VIII) and (IX), two or more of the groups represented by $R^2$-$R^{12}$, when present in the same structure, may be linked together to form a cyclic structure comprising at least one nitrogen atom. Suitable organic phase transfer catalysts having general structure (VII) are illustrated by hexaethylguanidinium mesylate, hexaethylguanidinium chloride, hexaethylguanidinium bromide, hexaethylguanidinium acetate, and combinations thereof. Suitable organic phase transfer catalysts having general structure (VIII) are illustrated by 1-neopentyl-4-(N,N-dibutylamino)-pyridinium chloride; 1-neopentyl-4-piperidin-1-ylpyridinium chloride; 1-neopentyl-4-piperidin-1-ylpyridinium mesylate; 1-3-methylheptyl-4-(4-methyl)-piperidin-1-ylpyridinium chloride, and combinations thereof. Suitable organic phase transfer catalysts having general structure (IX) are illustrated by octamethylphosphazenium chloride (p=0), octamethylphosphazenium bromide (p=0), dodecamethylphosphazenium chloride (p=1), dodecamethylphosphazenium mesylate (p=1), and mixtures thereof. The amount of organic phase transfer catalyst is typically used in an amount corresponding to from about 0.1 mole percent to about 10 mole percent based on the total number of moles of substituted phthalic anhydride employed.

In one embodiment, the organic phase transfer catalyst is a bisguanidinium salt having structure (X)

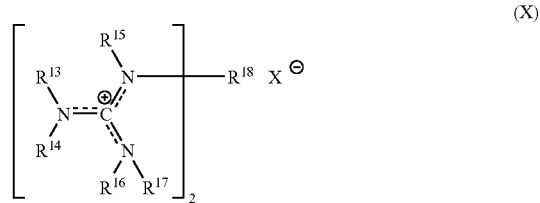
(X)

wherein each of $R^{13}$, $R^{14}$, $R^{15}$, $R^{16}$, $R^{17}$ and $R^{18}$ is independently $C_1$-$C_{20}$ aliphatic radical, a $C_3$-$C_{40}$ aromatic radical, or a $C_3$-$C_{20}$ cycloaliphatic radical. In addition two or more of $R^{12}$, $R^{13}$, $R^{14}$, $R^{15}$, $R^{16}$ and $R^{17}$ may together form a cycloaliphatic radical or an aromatic radical comprising at least one nitrogen atom. The anionic species, X⁻ (at times herein referred to as the "counterion"), represents one or more monovalent inorganic anions, monovalent organic anions, polyvalent inorganic anions, polyvalent organic anions, and mixtures thereof. Suitable organic phase transfer catalysts having structure (X) include the bisguanidinium salt wherein $R^{13}$, $R^{14}$, $R^{15}$, $R^{16}$, and $R^{17}$ are methyl groups, $R^{18}$ is a 1,3-propanediyl radical (i.e., —$CH_2CH_2CH_2$—), and $X^-$ represents two chloride anions.

In one embodiment, the inorganic carbonate salt has a structure (XI)

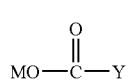

(XI)

wherein M is a metal ion selected from the group consisting of alkali metal ions, alkaline earth metal ions, and mixtures thereof, and Y is OM or OH. In one embodiment the metal ion M is lithium, sodium, potassium, or a mixture thereof. Suitable inorganic carbonates include potassium carbonate, sodium carbonate, potassium sodium carbonate, lithium carbonate, potassium lithium carbonate, sodium lithium carbonate, potassium bicarbonate, sodium bicarbonate, lithium bicarbonate, and mixtures thereof.

Typically, the inorganic carbonate and the substituted phthalic compound (VI) are employed in amounts corresponding to a ratio of the inorganic carbonate to substituted phthalic compound in a range from about 1.0 moles to about 1.5 moles of inorganic carbonate to about 1 mole of substituted phthalic compound (VI).

In one embodiment, the first product mixture, obtained as described above comprises at least 25 weight percent by weight of the oxybisphthalic compound. In another embodiment, the oxybisphthalic compound is present in the first product mixture in an amount corresponding to at least 35 percent by weight of a total weight of the first mixture. In yet another embodiment, the oxybisphthalic compound is present in the first product mixture in an amount corresponding to at least 50 percent by weight of a total weight of the first mixture. Typically, the first product mixture is a slurry in which a portion of the oxybisphthalic compound is dissolved in the solvent and a portion of the oxybisphthalic compound is present as a solid phase of the slurry. Owing to their generally poor solubility, the alkali metal halides and alkaline earth metal halides typically remain as solids within the first mixture. It will be understood by those skilled in the art that the word "mixture" as used herein refers to a combination of at least two components at least one of which is at least partially insoluble in the other. Thus each of the "first product mixture", the "second product mixture" and the "third product mixture" comprises at least one component that is at least partially insoluble. For example, in one embodiment, the "third product mixture" is a mixture in which essentially all of the oxybisphthalic compound is in solution, but at least a portion of the inorganic salt remains insoluble and is present as a solid phase component of the mixture. Typically, the inorganic salt is highly insoluble in the "third product mixture" allowing separation of the inorganic and organic components of the mixture by filtering off the inorganic salt.

The first product mixture is then diluted with at least one solvent to provide a second product mixture wherein the oxybisphthalic compound is present in an amount corresponding to less than 25 percent by weight of the total weight of the second product mixture. In another embodiment, the oxybisphthalic compound is present in an amount corresponding to less than 15 percent by weight of the total weight of the second product mixture. In yet another embodiment, the oxybisphthalic compound is present in an amount corresponding to less than 10 percent by weight of the total weight of the second product mixture. In one embodiment, the solvent employed in diluting the first product mixture is ortho-dichlorobenzene. In alternate embodiments the solvent employed is at least one solvent selected from the group consisting of chlorobenzene, para-dichlorobenzene, dichlorotoluene, 1,2,4-trichlorobenzene, diphenyl sulfone, phenetole, anisole, veratrole, toluene, xylene, mesitylene, and mixtures thereof. In yet another embodiment, the solvent employed comprises ortho-dichlorobenzene and at least one other aromatic solvent. Non-limiting examples of suitable aromatic solvents include toluene, mesitylene, xylene, etc.

In one embodiment of the present invention, essentially all of the oxybisphthalic anhydride present in the second product mixture is dissolved in the solvent to form a third product mixture (step (c)). Suitable solvents include those discussed herein, for example anisole, chlorobenzene, ortho-dichlorobenzene, etc. Typically, a single solvent is employed in each of steps (a)-(e) for preparing an oxybisphthalic compound. Ortho-dichlorobenzene is in certain instances a preferred solvent. Typically the dissolution of the oxybisphthalic anhydride (step (c)) is effected by heating the second product mixture to a temperature in the range from about 80° C. to about 220° C. in an embodiment, from about 100° C. to about 200° C. in another embodiment, and from about 130° C. to about 180° C. in still another embodiment. Upon dissolution of essentially all of the oxybisphthalic anhydride the "third product mixture" is formed. Typically, this third product mixture comprises less than 25 ppm of water. In one embodiment, the third product mixture comprises less than 15 ppm of water. In yet another embodiment, the third product mixture comprises less than 5 ppm of water. It is believed that it is generally preferable that the third product mixture contain as little water as possible. The presence of water in any of the steps used for preparing the oxybisphthalic compound is thought to contribute to water in the final oxybisphthalic compound product. Higher concentrations of water are thought to be the source of higher than desired levels of alkali metal ions in the product oxybisphthalic anhydride. In one embodiment, distillation of a portion of the solvent present in the third product mixture aids in removal of some of the water, thereby leading to the formation of a more concentrated third product mixture comprising less than 25 ppm water.

Next, the third product mixture is filtered to separate the insoluble inorganic salt from the dissolved oxybisphthalic compound. The filtration is carried out at a temperature above the crystallization point temperature of the oxybisphthalic compound in order to avoid crystallization within the device used to effect the filtration. As will be understood by those skilled in the art, the crystallization point temperature is a function of a number of parameters including the concentration of the dissolved oxybisphthalic compound in the solvent, the properties of the solvent, the structure of the oxybisphthalic compound, and the state of purity of the oxybisphthalic compound (e.g., mixtures of isomeric oxybisphthalic anhydrides versus single isomer oxybisphthalic anhydrides). The crystallization point temperature is typically in a range from about 0° C. to about 200° C. Typically, the filtration device is a porous filter that can be heated to maintain a temperature above the crystallization point temperature of the oxybisphthalic compound. In an embodiment, the filtration step yields a "first solution", that is a homogenous solution containing the oxybisphthalic compound, and a filter cake, the filter cake being comprised of the solid components of the third product mixture. The filter cake typically contains the inorganic salt as the major component together with a lesser amount of the oxybisphthalic compound. In an embodiment, from about 5 to about 10 weight percent of the total amount of oxybisphthalic compound present initially in the first product mixture forms part of the filter cake. In one embodiment the filtering is carried out at a temperature in a range from about 50° C. to about 250° C., in another embodiment from about 100° C. to about 225° C., and in yet another embodiment from about 125° C. to about 190° C. Typically, the filtering is carried out at (0 PSIG), near (5-25 PSIG) atmospheric pressure, or super-atmospheric pressure (for example at 25-100 PSIG) under an inert atmosphere, for example under a nitrogen atmosphere. A sub-atmospheric vacuum driving force filtration can also be carried out to effect separation of the solution and solids. Filtering may be carried out employing methods known in the art. In one embodiment, the filtering is carried out in a metal filter. In an alternate embodiment, the filtering is carried out in a ceramic filter. In one embodiment, the filter is a sintered metal filter having a pore size in a range from about 0.5 microns to about 5 microns. In various embodiments of the present invention, the filter employed has a pore size in a range from about 0.1 microns to about 10 microns, alternately from about 0.2 microns to about 5 microns.

The first solution comprises the oxybisphthalic compound, the organic phase transfer catalyst, and other impurities dissolved in an organic solvent. For example, when 4,4'-ODPA is produced from the HEGCl-catalyzed reaction of 4-chlorophthalic anhydride and potassium carbonate in ODCB, a significant amount of HEGCl, HEGCl degradation/reaction products, and amine color bodies are present in the first solution and remain in the 4,4'-ODPA product after crystallization from the first (ODCB) solution. Typically, the first solution comprises the organic phase transfer catalyst in an amount corresponding to from about 500 ppm to about 5000 ppm in an embodiment, from about 1000 ppm to about 3000 ppm in another embodiment, and from about 1000 ppm to about 2000 ppm in still another embodiment. Various techniques, such as ion chromatography (IC), high pressure liquid chromatography (HPLC), and nuclear magnetic resonance (NMR) spectroscopy can be used to quantitatively measure the amount of the organic phase transfer catalyst.

In accordance with an aspect of the present invention, the first solution is contacted with a solid inorganic adsorbent material to provide a second solution of the oxybisphthalic compound I, which is substantially free of the organic phase transfer catalyst. The contacting step may be carried out either in a continuous or a batch-wise manner. The term "contacting" herein refers to any combination of heating and stirring, or heating and flowing through a packed bed of a solid adsorbent. Thus in an embodiment, "contacting" comprises heating without stirring, in another embodiment, it refers to heating with stirring. Stirring with heating is generally preferred since it facilitates good contact of the surfaces of the adsorbent material with the organic phase transfer catalyst present in the solution phase. In another embodiment, the solution is passed through a single bed packed with solid adsorbent in batch mode, or through a series of packed beds to simulate counter-current "contacting" of solution and adsorbent. A variety of solid inorganic adsorbent materials can be used. The adsorption capacity of a solid inorganic adsorbent material depends upon, among other factors, the pore size (or pore diameter) and the cumulative pore volume distribution of the adsorbent particles. Pore size measurements can be made using any of the methods known in the art. Cumulative pore volume distribution can be obtained from the total cumulative pore volume, which in turn can be obtained from the total pore volume. Total pore volume is given by the sum of pore volumes of all adsorbent particles over the entire pore size range present in the adsorbent sample. Total cumulative pore volume for a given pore size (such as for example, particles having a pore size of less than about 3 nanometers, less than about 10 nanometers, less than about 20 nanometers, and the like) is expressed as a percentage of the total pore volume. The cumulative pore volume distribution for a given pore size or pore size range (such as for example, less than about 3 nanometers, from about 3 nanometers to about 10 nanometers, from about 3 nanometers to about 20 nanometers, and the like) in turn can be obtained from the total cumulative pore volume. Adsorbent materials that provide a mesoporous surface or a combination of mesoporous and microporous surfaces can be used. Microporous adsorbent materials have a pore size (hereinafter also expressed as "pore diameter") of less than about 3 nanometers. In another embodiment, adsorbent materials having a pore size of less than about 10 nanometers can be used. Mesoporous adsorbent materials having a pore size of less than 60 nanometers in an embodiment, in a range between about 10 nanometers and about 20 nanometers in another embodiment, and in a range between about 3 nanometers and 20 nanometers in still another embodiment, can also be used. Exemplary adsorbent materials include silica, alumina, zeolites, inorganic ion exchange compounds, and mixtures thereof. Some examples of inorganic ion exchangers include the aluminophosphate and aluminosilicate class of materials. Silica-based adsorbents are preferred since they generally have a higher capacity and selectivity for adsorbing the organic phase transfer catalyst. Silica adsorbents are found to have a more uniform pore size (or a narrower pore size distribution). Commercially available silica adsorbent materials are available which are sufficiently robust so that the pore structure of the silica will not collapse or degenerate when contacted with a polar medium such as water. In a preferred embodiment, the present invention employs a silica which is resistant to pore collapse when in contact with water during a regeneration step. Examples of suitable adsorbents include those available commercially from PQ Corporation, such as the C930 and R100 silicas; and CBV901 zeolite. It is typically preferable to dry the adsorbents prior to contacting the first solution with a solid inorganic adsorbent material. Drying of the solid inorganic adsorbent material can be accomplished by heating at temperatures between 150° C. to about 250° C. under vacuum. Adsorbent materials dried in this manner have significantly higher adsorption capacity for impurities such as the organic phase transfer catalyst, amine color bodies, and other impurities; and also a higher selectivity for adsorbing the phase transfer catalyst than the oxybisphthalic compound.

As noted, typically the contacting of the adsorbent material and the first solution is carried out at a temperature in a range between about 50° C. and about 250° C. in an embodiment, between about 80° C. and about 200° C. in another embodiment, and between about 100° C. and 160° C. in yet another embodiment. The organic phase transfer catalyst level in the first solution generally ranges from about 500 ppm to about 5000 ppm in an embodiment, from about 1000 ppm to about 3000 ppm in another embodiment, and from about 1000 ppm to about 2000 ppm in still another embodiment. In a further embodiment, the first solution contains the organic phase transfer catalyst at a level equal to that used in the reaction to form the oxybisphthalic compound, and can range from 5000-25000 parts per million. The first solution generally comprises less than or equal to about 25 weight percent of the oxybisphthalic compound. When an ODPA solution in ODCB is used, for example, the solution may comprise, in various embodiments, about 1 to about 25 weight percent, about 5 to about 15 weight percent, or about 5 to about 10 weight percent of ODPA.

In accordance with another aspect of the present invention, removal of organic phase transfer catalyst from the oxybisphthalic compound can also be accomplished by contacting a dry or a wet cake sample of the oxybisphthalic compound with a slurry of the solid inorganic adsorbent material in a suitable solvent. In this approach, the solid inorganic adsorbent material is first suspended in at least one solvent (e.g., ODCB) to give a slurry. The adsorbent is then allowed to equilibrate with the solvent. Equilibration of the adsorbent material is achieved by maintaining the contact of the solid inorganic adsorbent material with the solvent for about 1 hour in an embodiment, and for about 2 hours in another embodiment. Dry or wet oxybisphthalic compound (wet due to presence of residual organic solvent in the product from the reaction forming the oxybisphthalic compound) is then added to the slurry of the solid inorganic adsorbent material in the solvent and the resultant mixture is then allowed to equilibrate for a longer or shorter period a required. Typical equilibration times may range from less than a minute to several hours. In one embodiment, equilibration of the mixture of the first solution and the solid inorganic adsorbent material is carried out for 1 hour. In an alternate embodiment, a 2 hour equilibration period is used. In yet another embodiment, a 3 hours equilibration period is used. During the period of contact between the first solution and the solid inorganic adsorbent material, the organic phase transfer catalyst is adsorbed onto the solid inorganic adsorbent material, thereby reducing the level of dissolved phase transfer catalyst. The slurry prepared from the first solution and the solid inorganic adsorbent material is then filtered to furnish purified oxybisphthalic compound as a "second solution", from which the oxybisphthalic compound may be crystallized.

In one embodiment, the present invention provides a second solution of an oxybisphthalic compound having structure I, which is substantially free of organic phase transfer catalyst. Those skilled in the art will appreciate that crystallization of the oxybisphthalic compound from a second solution which is substantially free of organic phase transfer catalyst will result in a solid oxybisphthalic compound which is also substantially free of organic phase transfer catalyst. In one embodiment, crystallization of the oxybisphthalic compound from a second solution which is substantially free of organic phase transfer catalyst results in a slurry comprising the solid oxybisphthalic compound and a solvent, said slurry being substantially free of organic phase transfer catalyst. As used herein, the expression "substantially free of" means that the residual amount of organic phase transfer catalyst present is less than about 150 ppm. A second solution which is substantially free of organic phase transfer catalyst comprises less than about 150 ppm organic phase transfer catalyst. By way of further illustrating the meaning of "substantially free of organic phase transfer catalyst" as used herein, an oxybisphthalic compound (I) which is substantially free of organic phase transfer catalyst comprises less than about 150 ppm organic phase transfer catalyst; and an oxybisphthalic anhydride (IV) which is substantially free of organic phase transfer catalyst comprises less than about 150 ppm organic phase transfer catalyst.

In one embodiment, the present invention provides a purified oxybisphthalic compound having structure (I), wherein the purified oxybisphthalic compound is substantially free of organic phase transfer catalyst. In one embodiment, the present invention provides a purified oxybisphthalic compound (1) comprising less than about 150 ppm of the organic phase transfer catalyst. In an alternate embodiment, the present invention provides a purified oxybisphthalic compound (I) comprising from about 2 parts per million (ppm) to about 120 ppm of the organic phase transfer catalyst. In yet another embodiment, the present invention provides a purified oxybisphthalic compound (I) comprising from about 5 ppm to about 100 ppm of the organic phase transfer catalyst.

In one embodiment, the present invention provides a purified oxybisphthalimide having structure (II), wherein the purified oxybisphthalimide is substantially free of organic phase transfer catalyst. In one embodiment, the present invention provides a purified oxybisphthalimide (II) comprising less than about 150 ppm of the organic phase transfer catalyst. In an alternate embodiment, the present invention provides a purified oxybisphthalimide (II) comprising from about 2 parts per million (ppm) to about 120 ppm of the organic phase transfer catalyst. In yet another embodiment, the present invention provides a purified oxybisphthalimide (II) comprising from about 5 ppm to about 100 ppm of the organic phase transfer catalyst.

In one embodiment, the present invention provides a purified oxybisphthalic anhydride having structure (IV), wherein the purified oxybisphthalic anhydride is substantially free of organic phase transfer catalyst. In one embodiment, the present invention provides a purified oxybisphthalic anhydride (IV) comprising less than about 150 ppm of the organic phase transfer catalyst. In an alternate embodiment, the present invention provides a purified oxybisphthalic anhydride (IV) comprising from about 2 parts per million (ppm) to about 120 ppm of the organic phase transfer catalyst. In yet another embodiment, the present invention provides a purified oxybisphthalic anhydride (IV) comprising from about 5 ppm to about 100 ppm of the organic phase transfer catalyst.

After the adsorptive removal of organic phase transfer catalyst and other impurities by the solid adsorbent material, the adsorbent material may become "spent", i.e., it may not be able to adsorb any more, or a practically useful level of the organic phase transfer catalyst impurity. The spent adsorbent may be regenerated for reuse in the adsorption process. Regeneration can be accomplished by desorbing the organic phase transfer catalyst and the co-adsorbed oxybisphthalic compound using a polar liquid medium, such as water, preferably hot water; steam, methanol, ethanol, isopropanol, aliphatic and/or aromatic alcohols, aqueous acids, such as aqueous phosphoric acid, and the like. Hot water in the range of 40° C. to 100° C., or more preferably from 80° C. to 100° C. can be used. In another embodiment, superheated water at temperatures greater than 100° C. under pressure can be used. In other embodiments, the adsorbent may be regenerated with hot oxidizing gases such as air, oxygen, or carbon dioxide; with acids such as hydrochloric acid or sulfuric acid in temperature ranges from 100° C. to 300° C., preferably from 150° C. to 250° C., at atmospheric or elevated pressures. In a still another embodiment, the adsorbent can be regenerated using a supercritical gas, such as carbon dioxide.

As noted, the product oxybisphthalic compound may be further purified by crystallization from the second solution. Typically the crystallization is effected using conventional techniques that are well known in the art at a temperature corresponding to the crystallization point temperature or a lower temperature. Thus, crystallization of the oxybisphthalic compound from the homogenous second solution is typically effected at a temperature in a range from about 0° C. to about 200° C. In one embodiment, the crystallization is effected at a temperature in a range of from about 10° C. to about 120° C. In an alternate embodiment, crystallization is effected at a temperature in a range from about 10° C. to about 80° C. Typically, the crystallization is effected in a vessel equipped with an agitator. When the crystallization step is effected under agitation, the product of the crystallization step is a slurry of the crystallized oxybisphthalic compound in the solvent. Crystallized oxybisphthalic compound obtained in this manner typically comprises residual organic phase transfer catalyst. In one embodiment, the crystallized oxybisphthalic compound comprises less than about 100 ppm of the organic phase transfer catalyst. In an alternate embodiment, the crystallized oxybisphthalic compound comprises residual organic phase transfer catalyst in an amount corresponding to from about 1 ppm to about 90 ppm. In yet another embodiment, the crystallized oxybisphthalic compound comprises residual organic phase transfer catalyst in an amount corresponding to from about 1 ppm to about 10 ppm.

Those skilled in the art will understand that the purified oxybisphthalimides (I) may be converted into oxybisphthalic anhydrides having structure (IV) by hydrolysis to the corresponding tetraacid followed by ring closure to the dianhydride. Hydrolysis of the oxybisphthalimide (I) may be effected by various means, for example by heating the oxybisphthalimide (I) in aqueous sodium hydroxide. The hydrolysis product, a tetra sodium carboxylate, may be neutralized with a strong acid, for example hydrochloric acid, to produce the corresponding tetraacid which precipitates from solution. The tetraacid intermediate may be isolated, for example by filtration, and thereafter subjected to ring closure of the tetraacid to the corresponding dianhydride. In one embodiment, ring closure of the tetraacid to the corresponding dianhydride is effected by heating the tetraacid to a temperature above its melting point and driving off water.

The oxybisphthalic anhydrides purified by the method of the instant invention are valuable for preparing polyetherimides. In one aspect then the present invention provides a method comprising combining at least one solvent, at least one purified oxybisphthalic anhydride, and at least one diamino aromatic compound to form a polymerization mixture under art-recognized conditions suitable for the condensation polymerization of an oxybisphthalic anhydride with an aromatic diamine. Typically, such conditions involve heating a solution of roughly equal molar amounts of the oxybisphthalic anhydride and diamine in the presence of an imidization catalyst such as sodium phenylphosphinate (SPP, $C_6H_5PO_2Na$). The polymerization reaction is generally conducted under conditions such that the solvent is continuously refluxing. A trap such as a Dean-Stark trap may be employed to separate water formed during the condensation polymerization. In general, the polymerization reaction is most efficient and higher molecular weight polyetherimide product is obtained when as much water as possible is removed from the reaction mixture.

In one embodiment, the at least one diamino aromatic compound may be represented by formula (XII)

(XII) $H_2N$—B—$NH_2$ wherein B is a $C_3$-$C_{30}$ divalent aromatic radical. In one embodiment B is a monocyclic divalent aromatic radical, for example paraphenylene, metaphenylene, or combinations thereof. In an alternate embodiment B is a polycyclic divalent aromatic radical, for example 4,4'-biphenylene or 1,4-naphthalene.

In one embodiment B is a $C_3$-$C_{30}$ divalent aromatic radical having structure

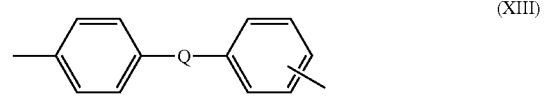

(XIII)

wherein the unassigned positional isomer about the aromatic ring is either ortho, meta or para to Q, and Q is a linking group chosen from

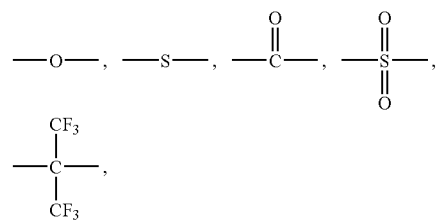

a covalent bond, an alkylene group of the formula $C_yH_{2y}$, or an alkylidene group of the formula $C_yH_{2y}$; wherein "y" is an integer from 1 to 5 inclusive. In some particular embodiments "y" has a value of one or two. Illustrative alkylene and alkylidene linking groups Q include, but are not limited to, methylene, ethylene, ethylidene, propylene, and isopropylidene. In other particular embodiments the unassigned positional isomer about the aromatic ring in formula (XIII) is para to Q.

In certain embodiments, the two amino groups present in diamino aromatic compound XII are separated by at least two and sometimes by at least three ring carbon atoms. For example, the amino groups present in meta-phenylene diamine are separated by three ring carbon atoms. By way of further example, the amino groups present in para-phenylene diamine are separated by four ring carbon atoms. When the amino group or groups are located in different aromatic rings of a polycyclic aromatic moiety comprising structure (XIII), they are often separated from the linking group Q between by at least three ring carbon atoms.

Diamino aromatic compounds XII are illustrated by 2-methyl-1,3-diaminobenzene; 4-methyl-1,3-diaminobenzene; 2,4,6-trimethyl-1,3-diaminobenzene; 2,5-dimethyl-1,4-diaminobenzene; 2,3,5,6-tetramethyl-1,4-diaminobenzene; 1,2-bis(4-aminoanilino)cyclobutene-3,4-dione, bis(4-aminophenyl)-2,2-propane; bis(2-chloro-4-amino-3,5-diethylphenyl)methane, 4,4'-diaminodiphenyl, 3,4'-diaminodiphenyl, 3,3'-diaminodiphenyl, 3,3'-dimethyl-4,4'-diaminodiphenyl, 3,3'-dimethoxy-4,4'-diaminodiphenyl, 2,2',6,6'-tetramethyl-4,4'-diaminobiphenyl; 3,3'-dimethoxy-4,4'-diaminobiphenyl; 4,4'-diaminodiphenylmethane, 3,3'-diaminodiphenylmethane, 3,4'-diaminodiphenylmethane, 1,3-bis(3-aminophenoxy)benzene, 1,3-bis(4-aminophenoxy)benzene, 1,4-bis(4-aminophenoxybenzene), bis(4-(4-aminophenoxy)phenyl)sulfone, bis(4-(3-aminophenoxy) phenyl)sulfone, 4-(4-aminophenoxy)phenyl)(4-(3-aminophenoxy)phenyl)sulfone, 4,4'-bis(3-aminophenoxy) biphenyl, 4,4'-bis(4-aminophenoxy)biphenyl, 4-(3-aminophenoxy)-4'-(4-aminophenoxy)biphenyl, 2,2'-bis(4-(4-aminophenoxy)phenyl)propane, 2,2-bis[4-(4-aminophenoxy)phenyl]hexafluoropropane, 4,4'-bis (aminophenyl)hexafluoropropane, 4,4'-diaminodiphenyl ether, 3,4'-diaminodiphenyl ether, 3,3'-diaminodiphenyl ether, 4,4'-diaminodiphenylsulfide, 3,4'-diaminodiphenylsulfide, 3,3'-diaminodiphenylsulfide, 3,3'-diaminodiphenylsulfone, 4,4'-diaminodiphenyl sulfone, 3,4'-diaminodiphenyl sulfone, 4,4'-(9-fluorenylidene)dianiline; 4,4'-diaminodiphenyl ketone, 3,4'-diaminodiphenyl ketone, 3,3'-diaminodiphenyl ketone, 2,6-diaminotoluene and 2,4-diaminotoluene.

In one embodiment, two or more diamino aromatic compounds can also be used. For example, the ETHACURE diamines, available from Albemarle Corporation, Baton Rouge, La., such as ETHACURE 100, which is a 80:20 weight ratio combination of 2,6-diethyl-4-methyl-1,3-phenylene diamine and 4,6-diethyl-2-methyl-1,3-phenylene diamine, respectively; and ETHACURE 300 which is a 80:20 weight ratio combination of 2,6-bis(mercaptomethyl)-4-methyl-1,3-phenylenediamine and 4,6-bis(mercaptomethyl)-2-methyl-1,3-phenylene diamine, respectively, can also be used. Perfluorinated alkyl or partially fluorinated alkyl analogs of said diamines are also suitable for use.

EXAMPLES

The following examples are set forth to provide those of ordinary skill in the art with a detailed description of how the methods claimed herein are evaluated, and are not intended to limit the scope of what the inventors regard as their invention.

Reagent grade ODCB was used for all experimental studies, and was dried to specific water levels by distillation at reflux conditions. Water levels in the ODCB were measured by Karl Fischer analysis using 500 microliters of distilled ODCB samples.

Adsorbents were received from the manufacturer and dried to constant weight in a vacuum oven maintained at 160° C. and reduced pressure (380 mm Hg). Silica samples were dried by suspending them in ODCB and distilling out the ODCB to facilitate removal of water.

A low temperature nitrogen adsorption technique was used to probe the adsorbent surface. By employing the Brunauer-Emmett-Teller (BET) equation for isotherms, which depend on the partial pressure and vapor pressure of the adsorbate, and the Barret-Joyner-Halenda (BJH) method for pore size analysis, the pore volume and pore surface area, as a function of pore diameter (pore size) was developed. Using the BJH method in conjunction with the BET adsorption and desorption isotherms at −196° C. (77° K) for nitrogen on the adsorbent, a pore size distribution for the adsorbent was determined.

Oxydiphthalic anhydride (ODPA) samples containing HEGCl phase transfer catalyst were received as wet solids due to the presence of ODCB in the samples. The samples were dried to constant weight in a vacuum oven maintained at 160° C. and reduced pressure (380 mm Hg). HEGCl levels were measured by an HPLC technique using a Agilent Zorbax SB-C-18 4.6×75 mm 3.5μ HPLC column that was maintained at 25° C. A 0.1 gram sample of dry ODPA was taken in a vial and treated with 5 milliliters of a solution of acetonitrile containing 0.288 milligram of phenanthrene (internal standard). The mixture was heated to about 90° C. for 1-3 minutes to obtain a homogeneous solution, which was filtered. A 4-microliter sample of the filtrate was used for the HPLC analysis. Aqueous $H_3PO_4$ was prepared by taking 3 milliliters of concentrated $H_3PO_4$ (85% $H_3PO_4$ in water) and diluting to 3800 milliliters total volume using deionized water.

TABLE 1

| Elution Time (min) | Flow (ml/min) | $CH_3CN$ (volume percent) | Aqueous $H_3PO_4$ (volume percent) | Methanol (volume percent) |
|---|---|---|---|---|
| 0 | 1.5 | 40 | 59 | 1 |
| 10 | 1.5 | 40 | 59 | 1 |
| 14 | 1.5 | 90 | 0 | 10 |
| 16 | 1.5 | 40 | 59 | 1 |
| 20 | 1.5 | 40 | 59 | 1 |

Example 1

This Example describes the general procedure used for batch adsorption experiments using C-930 silica (available from PQ Corporation) as the adsorbent material.

The required amounts of ODPA containing a known amount of HEGCl and pre-dried silica samples were weighed out separately so as to achieve a desired ODPA/silica weight ratio. The silica sample was added to pre-dried ODCB solvent to provide approximately a 5 weight percent slurry. The slurry was heated and maintained at a constant temperature of 140° C., 150° C., or 160° C. with stirring for 1-2 hours to allow for temperature equilibration prior to adding ODPA. To this slurry was added the ODPA as a dry solid. When all the ODCB had dissolved, the resulting slurry of silica in ODPA/ODCB solution was equilibrated for 3 hours by stirring at the desired temperature, 140° C., 150° C., or 160° C. The slurry was hot filtered using a 0.5-micron sintered metal filter heated to about 170° C. This removed the adsorbent from the ODPA solution. To maximize the recovery of purified ODPA, the filter cake was washed with hot ODCB at 160° C. to remove any ODPA present in the adsorbent filter cake. The filtrate was then cooled and crystallized while mixing. The resulting ODPA crystals were isolated from the slurry on a Buchner funnel using filter paper. The filter cake was washed with ODCB to displace mother liquor remaining in the ODPA wet cake. The washed filter cake was then dried to constant weight in a vacuum oven maintained at 160° C. and reduced pressure (380 mm Hg). The mother liquor was analyzed for HEGCl and residual ODPA. Residual HEGCl content in the dried ODPA was also measured. Material balances with respect to ODPA and HEGCl were generally greater than 95 weight percent. Results from the adsorptive purification experiments are shown in Table 2.

TABLE 2

| Example Number | ODPA/Silica weight ratio | Moisture in silica adsorbent (ppm) | HEGCl in feed ODPA (ppm) | HEGCl in purified ODPA (ppm) | HEGCl adsorbed by silica (weight percent of initial HEGCl level) | Isolated yield of purified ODPA (weight percent) |
|---|---|---|---|---|---|---|
| 2 | 7.3 | 10 | 1126 | 90 | 87 | 97 |
| 3 | 3.8 | 10 | 1446 | 44 | 94 | 95 |

TABLE 2-continued

| Example Number | ODPA/Silica weight ratio | Moisture in silica adsorbent (ppm) | HEGCl in feed ODPA (ppm) | HEGCl in purified ODPA (ppm) | HEGCl adsorbed by silica (weight percent of initial HEGCl level) | Isolated yield of purified ODPA (weight percent) |
|---|---|---|---|---|---|---|
| 4 | 4 | 40 | 1237 | 9 | 98 | 93 |
| 5 | 2 | 10 | 1335 | 10 | 99 | 85 |
| 6 | 4 | 10 | 1236 | 4 | 99 | 92 |
| 7 | 4 | 10 | 1399 | 40 | 97* | 93* |
| 8 | 1.3 | 10 | 1335 | 4 | >99 | 79 |

Indicates that the silica adsorbent obtained from the 1st treatment cycle was regenerated and used for a second batch purification of ODPA.

The results in Table 2 show that pre-dried silica is effective in removing HEGCl from ODPA prepared using HEGCl as a phase transfer catalyst.

The procedure of Example 1 was used with C-930 Silica and other adsorbents, such as R-100 Silica, CBV901 zeolite, BG-HHM Carbon, Calgon RB Carbon, and Calgon BL Carbon. Table 3 shows the HEGCl adsorption capacity (milligrams per gram), total pore volume (milliliters per gram), and cumulative pore volume distribution, which is expressed as a percent of the total pore volume, and as a function of the pore diameter range (expressed in nanometers) of the adsorbent particles. The results show that silica and zeolite adsorbents which have a total pore volume of 0.5 milliliters/gram or greater, and a cumulative pore volume distribution of about 20 percent or greater of particles having a pore diameter in a range between about 3 nanometers and about 20 nanometers are more effective in adsorbing HEGCl from a solution of ODPA.

TABLE 4

| Example Number | Regeneration Solution | T (° C.) | Wt % HEGCl/ODPA loaded silica in solvent | pH | Mass Desorbed (wt % of initial) |
|---|---|---|---|---|---|
| 14 | ODCB | 170 | 19.75 | NA | 5.7 |
| 15 | $H_3PO_4/H_2O$ | 100 | 8.51 | 1.3 | 26.2 |
| 16 | $H_2O$ | 100 | 9.14 | 6.0 | 27.4 |
| 17 | 2-propanol | 82 | 8.93 | ~7 | 10.1 |

Thermo-gravimetric analysis (TGA) was carried out to determine the amount of HEGCl and ODPA adsorbed on the "spent" C-930 silica sample. The sample was heated from an initial temperature of 20° C. to 800° C. in air to thermally desorb the HEGCl and ODPA from the silica surface. The above procedure was also repeated with a clean sample of commercial silica C-930 sample and used as a blank.

TABLE 3

| Example Number | Adsorbent | HEGCl Capacity | Total pore volume | Total surface area | Cumulative pore volume distribution (%, as a function of pore diameter range of adsorbent particles) | | | | | |
|---|---|---|---|---|---|---|---|---|---|---|
| | | | | | <3 nm | 3- 10 nm | 10- 20 nm | 20- 30 nm | 30- 60 nm | >60 nm |
| 9 | C-930 Silica | 124.4 | 1.42 | 453 | 10.6 | 45.2 | 41.4 | 1.1 | 0.7 | 1 |
| 10 | R-100 Silica | 91.5 | 0.55 | 277 | 7 | 37.8 | 48.1 | 3.4 | 2.1 | 1.5 |
| 11 | CBV901 Zeolite | 21.9 | 0.5 | 676 | 55.7 | 10.7 | 8.5 | 5.5 | 13.9 | 5.3 |
| 12 | Calgon RB Carbon | 0.4 | 0.85 | 1343 | 68.2 | 15.4 | 6.2 | 2.5 | 4.6 | 2.9 |
| 13 | Calgon BL Carbon | 0.3 | 0.59 | 1005 | 73 | 13.2 | 5.7 | 2 | 3.8 | 1.8 |

Examples 14-17

Examples 14-17 illustrate regeneration of "spent" solid inorganic adsorbent material. The procedures are illustrated for Silica C-930 adsorbent that contained HEGCl and ODPA. The "Spent" Silica C-930 was boiled in an excess of water, 2-propanol, water containing 4 weight percent of phosphoric acid, or ODCB (maintained at 170° C.) for 2 hours. In each case, the slurry was filtered and the amount of HEGCl and ODPA present in the filtrate was measured. Then the amount of HEGCl desorbed from the silica was calculated. The data is shown in table 4. "NA" stands for "not applicable." The data shows that all the solvents are capable of desorbing HEGCl and ODPA from the silica, however, water and aqueous phosphoric acid are relatively more effective.

Example 18

Preparation of Polyetherimide from Purified 4,4'-ODPA.

A 1-liter glass reactor equipped with a mechanical agitator and an overhead condenser system adapted for removing a distillate was charged with 1,2-dichlorobenzene (565 grams), 4,4'-ODPA (purified by treating 4,4'-ODPA having 1086 ppm HEGCl with C-930 silica to a purified 4,4'-ODPA having 6 ppm of HEGCl, 74.6 grams), bisphenol A dianhydride (6.5 grams), meta-phenylene diamine (18.2 grams), para-phenylene diamine (7.8 grams), and aniline (1.8 grams). The reactor flask was immersed in a hot oil bath and the contents of the reactor were heated with stirring to a temperature of 180° C. to 190° C. 1,2-ODCB solvent and water from imidization were collected as a distillate over a period of about 12 hours. No stoichiometric adjustments of the various reactants were needed. After the reaction flask was cooled, the polymer was isolated by filtration and oven-dried. The final polymer material had 0.21 mole percent of net anhydride functional groups.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A method of preparing a polyetherimide, said method comprising reacting at least one aromatic diamine with a purified oxybisphthalic anhydride, said purified oxybisphthalic anhydride having structure (IV)

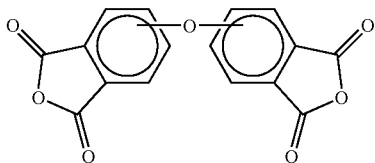

(IV)

said oxybisphthalic anhydride having been purified by a method, said method comprising the steps of:
  a. providing a first solution comprising at least one oxybisphthalic anhydride (IV), at least one solvent, and at least one organic phase transfer catalyst; and
  b. contacting the first solution with a solid inorganic adsorbent material, said solid inorganic adsorbent material having a total pore volume of about 0.5 milliliters/gram or greater, and a cumulative pore volume distribution of about 20 percent or greater of particles having a pore diameter in a range between about 3 nanometers and about 20 nanometers; to provide a second solution of the oxybisphthalic anhydride (IV), which is substantially free of the organic phase transfer catalyst.

2. The method of claim 1, wherein said contacting is carried out at a temperature in a range between about 50° C. and about 250° C.

3. The method of claim 1, further comprising crystallizing the oxybisphthalic anhydride (IV) from the second solution to provide a purified slurry of oxybisphthalic anhydride containing less than about 150 parts per million of an organic phase transfer catalyst.

4. The method according to claim 1, wherein the oxybisphthalic anhydride is selected from the group consisting of 4,4'-oxybisphthalic anhydride; 3,3'-oxybisphthalic anhydride; and mixtures thereof.

5. The method according to claim 1, wherein the oxybisphthalic anhydride is selected from the group consisting of 4,4'-oxybisphthalic anhydride; 3,4'-oxybisphthalic anhydride; and mixtures thereof.

6. The method according to claim 1, wherein the oxybisphthalic anhydride is selected from the group consisting of 3,4'-oxybisphthalic anhydride; 3,3'-oxybisphthalic anhydride; and mixtures thereof.

7. The method according to claim 1, wherein said oxybisphthalic anhydride has structure (V)

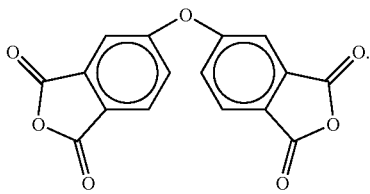

(V)

8. The method according to claim 1, wherein said at least one solvent is selected from the group consisting of chlorobenzene, ortho-dichlorobenzene, para-dichlorobenzene, dichlorotoluene, 1,2,4-trichlorobenzene, diphenyl sulfone, phenetole, anisole, veratrole, toluene, xylene, mesitylene, and mixtures thereof.

9. The method according to claim 1, wherein said at least one solvent is ortho-dichlorobenzene.

10. The method according to claim 1, wherein said solid inorganic adsorbent material is selected from the group consisting of silica, alumina, zeolites, inorganic ion exchange compounds, and mixtures thereof.

11. The method according to claim 1, wherein said solid inorganic adsorbent material is silica.

12. The method according to claim 1, wherein said solid inorganic adsorbent material is alumina.

13. The method according to claim 1, wherein said solid inorganic adsorbent material has a cumulative pore volume distribution of about 20 percent or greater of particles having a pore diameter in a range between about 10 nanometers and about 20 nanometers.

14. The method according to claim 1, wherein said organic phase transfer catalyst is present in said first solution in an amount corresponding to between about 0.1 and 10 mole percent based on the amount of the oxybisphthalic anhydride initially present.

15. The method according to claim 1, wherein said organic phase transfer catalyst is present in said second solution in an amount corresponding to from about 2 parts per million to about 120 parts per million.

16. A method of preparing a polyetherimide, said method comprising reacting at least one aromatic diamine with a purified oxybisphthalic anhydride, said purified oxybisphthalic anhydride having structure (IV)

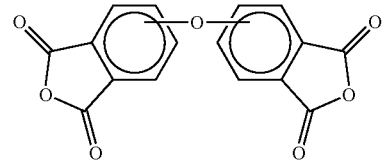

(IV)

said oxybisphthalic anhydride having been purified by a method, said method comprising the steps of:
  a. providing a first solution comprising at least one oxybisphthalic anhydride (IV), ortho-dichlorobenzene solvent, and a hexaalkylguanidinium halide phase transfer catalyst; and
  b. contacting the first solution with a silica, said silica having a total pore volume of about 0.5 milliliters/gram or greater, and a cumulative pore volume distribution of about 20 percent or greater of particles having a pore diameter in a range between about 3 nanometers and about 20 nanometers; said contacting being carried out at a temperature in a range between about 50° C. and about 250° C. to provide a second solution of the oxybisphthalic anhydride (IV) which is substantially free of said phase transfer catalyst.

17. The method of claim 16, further comprising crystallizing the oxybisphthalic anhydride (IV) from the second solution to provide a purified oxybisphthalic anhydride containing less than about 150 ppm of said phase transfer catalyst.

18. A method of preparing a polyetherimide, said method comprising reacting at least one aromatic diamine with a purified oxybisphthalic anhydride, said purified oxybisphthalic anhydride having structure (IV)

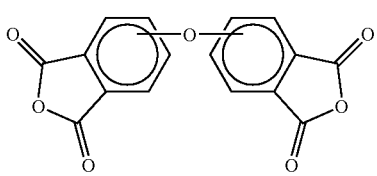
(IV)

said oxybisphthalic anhydride having been prepared by a method, said method comprising the steps (a)-(e)

a. contacting in a reaction mixture at least one substituted phthalic anhydride in at least one solvent in the presence of at least one organic phase transfer catalyst and at least one inorganic carbonate salt to provide a first product mixture comprising at least one oxybisphthalic anhydride, at least one solvent, and at least one inorganic salt selected from the group consisting of alkali metal halide salts, alkaline earth metal halide salts, and mixtures thereof, said oxybisphthalic anhydride being present in said first product mixture in an amount corresponding to at least 25 percent by weight of a total weight of said first product mixture, said substituted phthalic anhydride having structure VI

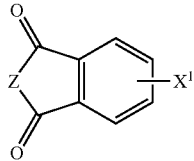
(VI)

wherein Z is O and $X^1$ is selected from the group consisting of fluoro, chloro, bromo, iodo, and nitro groups;

b. diluting said first product mixture with at least one solvent, to provide a second product mixture, wherein the oxybisphthalic anhydride is present in an amount corresponding to less than 25 percent by weight of a total weight of the second product mixture;

c. dissolving substantially all of the oxybisphthalic anhydride present in the second product mixture to provide a third product mixture, said third product mixture comprising less than 25 ppm water, and wherein said oxybisphthalic anhydride is present in an amount corresponding to less than 25 percent by weight of a total weight of the third product mixture; and d. filtering the third product mixture at a temperature above the crystallization point temperature of the oxybisphthalic anhydride to provide a first solution of the oxybisphthalic anhydride; and e. contacting the first solution with a silica, said silica having a total pore volume of about 0.5 milliliters/gram or greater, and a cumulative pore volume distribution of about 20 percent or greater of particles having a pore diameter in a range between about 3 nanometers and about 20 nanometers, said contacting being carried out at a temperature in a range between about 50° C. and about 250° C. to provide a second solution of the oxybisphthalic anhydride IV which is substantially free of said organic phase transfer catalyst.

19. The method of claim 18, further comprising crystallizing the oxybisphthalic anhydride IV from the second solution to provide a purified oxybisphthalic anhydride containing less than about 150 ppm of said organic phase transfer catalyst.

* * * * *